US006221316B1

(12) United States Patent
Hänggi et al.

(10) Patent No.: US 6,221,316 B1
(45) Date of Patent: Apr. 24, 2001

(54) USE OF BLENDS OF WATER-RESISTANT AND BIODEGRADABLE POLYMERS MADE FROM RENEWABLE FEEDSTOCKS WITH INCREASED BINDING AFFINITY FOR THE PRODUCTION OF CARRIERS FOR ANALYTIC SYSTEMS

(75) Inventors: Urs J. Hänggi, Forst-Kasten-Str. 15, D-82152 Krailling; Elvira Schecklies, Hebertshausen, both of (DE)

(73) Assignee: Urs J. Hänggi, Krailling (DE)

( * ) Notice: Subject to any disclaimer, the term of this patent is extended or adjusted under 35 U.S.C. 154(b) by 0 days.

(21) Appl. No.: 09/212,254

(22) Filed: Dec. 16, 1998

(30) Foreign Application Priority Data

Dec. 16, 1997 (DE) .............................................. 197 55 966

(51) Int. Cl.[7] ...................................................... B01L 3/00
(52) U.S. Cl. .......................... 422/102; 422/100; 264/330; 264/331.11
(58) Field of Search ............................. 422/91, 99–104; 436/86; 264/330, 331.11

(56) References Cited

U.S. PATENT DOCUMENTS 5,286,629 * 2/1994 Denis et al. ........................... 435/7.1
5,650,330 * 7/1997 Reusch ................................. 436/148

FOREIGN PATENT DOCUMENTS

| 0753539 | 1/1997 | (EP) . |
| 5-34343 | 2/1993 | (JP) . |
| WO94/06866 | 3/1994 | (WO) . |

* cited by examiner

*Primary Examiner*—Lyle A. Alexander
(74) *Attorney, Agent, or Firm*—Wenderoth, Lind & Ponack, L.L.P.

(57) ABSTRACT

The invention relates to the use of blends of biodegradable polymers made from renewable resources for the production of carrier systems for analytical tests. Blends of biodegradable polymers such as PHB (polyhydroxy butyrate) or PLA (polylactide) were found suitable for systems. They are available commercially. The formulations have affinities to organic molecules similar to that of the currently used polystyrene, and can be transformed as the latter on plastic injection moulding and processing machines into the same type of carriers for chemical, physical, enzymatic or immunological test systems. Application of PHB and PLA formulations according to the invention provides important advantages over using polystyrene as matrix substance: after use, the carriers can be composted or enzymatically degraded without the need of expensive disposal in landfill sites. In addition they are made from renewable resources and do not increase the carbon dioxide content of the atmosphere, even when burned.

14 Claims, No Drawings

USE OF BLENDS OF WATER-RESISTANT AND BIODEGRADABLE POLYMERS MADE FROM RENEWABLE FEEDSTOCKS WITH INCREASED BINDING AFFINITY FOR THE PRODUCTION OF CARRIERS FOR ANALYTIC SYSTEMS

The invention relates to the use of blends of biodegradable polymers made from renewable raw materials for manufacturing carrier systems for analytical test procedures.

Carriers for immunological, enzymatic, chemical, or physical analysis procedures are manufactured from petrochemical plastics, mainly from polystyrene. Examples of such carrier systems, but which do not cover the full range of test systems, are micro well plates, test rods, test tubes, or test spheres. The plastics used are characterized by for their resistance to water and their selective affinity to organic substances. Where appropriate, the surfaces of the carriers are modified physically or chemically, so that binding of the organic substance is more selective. The organic substances which are bound selectively may be molecules that differ with regard both to their composition and to their size. The molecules may be polar or non-polar, and the size of molecules may vary from several hundred thousand Dalton to just a few hundred. For analysis the molecules are bonded adhesively or covalently by well-known procedures. Known organic substances that bind to the carrier matrix are proteins, peptides, saccharides or polynucleotides.

Plastics suitable for use as carriers usually are melted in injection moulding or other plastic processing machines, and then, as molten mass, formed into the required shape and cooled. Once solidified, optionally, following further surface treatments, the items are sold in large quantities to analytic laboratories. The carriers, such as micro titre plates, test rods, test tubes and test spheres, are used in these laboratories for chemical, enzymatic, physical, or immunological tests either immediately, or after surface treatment with chemical reagents. For reasons of reproducibility of the analytical results, or for reasons of hygiene, the carrier systems usually are used only once and then, optionally after being autoclave sterilised, thrown away. Because of the large number of analytical tests, problems arise with the disposal of the carrier systems used. For reasons of hygiene, and because of the very many different substances that may adhere to the carriers after their use in analysis procedures, the polymer materials cannot be re-used by melting and recycling in order to make new carriers. In the best case scenario the chemical energy stored in the polymers can be utilised by combustion. However, the waste materials usually have to be taken to landfill waste disposal sites some distance away, and disposed of at great expense. In addition, the polymers are manufactured from mineral oil derivatives. Disposal, whether by combustion or by depositing at landfill sites, thus destroys these resources which is contrary to the principle of sustainability. Therefore the task of the inventors was to find alternatives to prevent the accumulation of large quantities of plastic waste from analysis laboratories, and at the same time, to comply with the principle of sustainability.

Similar to the materials currently used for producing carriers the polyesters PHB (polyhydroxybutyrate), a polymer of the polyalcanoate group, and PLA (polylactate) both are water-resistant and can be moulded as thermoplasts. Both PHB and PLA are well-known polymers obtained from renewable resources. They usually are compounded (mixed, blended) for injection moulding with other substances such as plasticisers, dyes, nucleation agents, and/or other additives which are customary in polymer chemistry. PHB or PLA formulations usually are used to produce injection moulded articles for medical purposes or in the environmental and packaging industries. There are two main reasons for using PHB or PLA formulations to manufacture articles: first the polymers are derived from sustainable resources, and second, the articles can be disposed of easily by biodegradation. Biodegradation occurs under composting conditions. Degradation can also occur as a purely enzymatic process. Examples for enzyme systems for enzymatic degradation have been described, for instance, in J. Environm. Polym. Degrad. 3, (1995), 187–197 or in the German patent application DE 4415127 A1. The latter patent application refers to the disposal of laboratory items manufactured from biodegradable raw materials.

It is known that proteins bind to PHB. Its protein binding characteristics are described in Biochemica et Biophysica Acta, 1123 (1992) 33–40 and Eur. Polymer. J. 30 (1994) 1327–1333. However the affinity is not sufficient for analytical purposes. Surprisingly it was found that certain formulations (blends) of PHB and PLA showed considerably higher affinities than the original polymers to organic substances such as, for example, proteins, peptides, saccharides, and polynucleotides. The binding characteristics of these formulations are comparable to the affinities of the polymers currently used for manufacturing test system carriers, in particular of polystyrene. The polymer formulations invented are blends of PLA with 0–95% PHB, optionally combined with other substances such as plasticisers, dyes, nucleation agents, and/or other additives which are customary in polymer chemistry. The base polymer PLA can be bought from several producers, for example from Neste Oy, Espoo, Finland; Cargill, Minnetoka, Minn., USA; Shimazu, Tokyo, Japan; or Boehringer Ingelheim, Ingelheim, Germany. The base polymer PHB can be obtained commercially from Monsanto, Louvain-La-Neuve, Belgium, from Metabolix, Cambridge, Mass. USA, or from Biomer, Krailling, Germany. The PLA and PHB blends described therein can be obtained commercially from Biomer, Krailling, Germany. The formulations are composed primarily of biological raw materials and they are fully biodegradable under compost conditions. The inorganic components used in the formulations are biologically inert. Therefore no expensive and difficult waste collection and disposal system is required for the formulations described therein. The carriers produced can be disposed of close to the user's premises like other organic (food or feed) wastes, and can be composted together with the other organic wastes. Since they are produced essentially from biogenic resources, they do not upset the $CO_2$ balance of the atmosphere, even when burned.

Thus, the subject of this invention is a carrier system for use in immunological, enzymatic, chemical, and physical tests, such as for example, but not exclusively, micro well plates, test rods, test tubes, test spheres, or other media. As opposed to the carrier systems currently available, these are fully biologically degradable, i.e. compostable, are manufactured from renewable resources, and demonstrate increased affinities to organic substances such as proteins, peptides, saccharides, and polynucleotides. They compare well with polymer carriers used at present, in particular carriers made of polystyrene. Like other polymers, the formulations can be obtained as pellets, and, like other polymers, they can be processed using standard plastic processing techniques. For example the pellets can be molten in injection moulding machines, pressed into shape as molten mass, and once solidified, sold to analytical laboratories where they can be used for analysis in the same way as the present carrier systems. The advantage of this invention is that the materials are manufactured from renewable raw materials. A further advantage is that the carrier systems used can be disposed of, possibly after an autoclave sterilisation process, either in waste combustion plants without adding $CO_2$ to the atmosphere, or by a simple composting process at local sites, or by means of enzymatic degradation.

The preferred use of the described PHB and PLA blends is for carriers for analytical test systems, in particular enzymatic, chemical, physical, or immunological test systems (ELISA) in the form of, but not exclusively, micro well plates, test rods, test tubes, and test spheres. Users can expect cost savings as a result of such options as enxymatic degradation or biodegradation by using the PHB and PLA formulations.

The examples below illustrate the affinity of different organic materials to the blends that are the subject of the specifications described therein. The organic substances were selected in order to indicate the type of applications for which the blends can be used but there is no restriction to these substances alone.

EXAMPLES

Example 1

Production of PHB/PLA Blends

PHB was mixed with varying quantities of PLA from different manufacturers (see table), together with 20% plasticiser (triacetine or tributylcitrate) and 0.5% nucleation agent (boron nitride), melted in an extruder, and formed into beads. Screw temperatures were 165° C. (Zone 1), 190° C. (Zone 2), 165° C. (Zone 3) and 135° C. (nozzle).

|  | Concentration of PLA | Manufacturer |
|---|---|---|
| Sample 1 | 5 | Boehringer Ingelheim, Ingelheim, Germany |
| Sample 2 | 10 | Boehringer Ingelheim, Ingelheim, Germany |
| Sample 3 | 10 | Shimazu Corp., Tokyo, Japan |
| Sample 4 | 10 | Mitsui Toatsu, Tokyo, Japan |
| Sample 5 | 100 | Shimazu Corp., Tokyo, Japan |

Example 2

Binding of Proteins to Biogenic and Biodegradable Carrier Materials

The beads obtained from example 1 were incubated overnight in a refrigerator with 50 μg/ml Immunoglobulin G (IgG) in phosphate buffered 0.7% salt solution (PBS). Then the beads were blocked at room temperature with 1% of albumin in PBS. After 2 hours, the blocking solution was removed, and the beads were incubated with protein A-linked alkaline phosphatase in PBS for 30 minutes at room temperature, then washed in distilled water, followed by 60 minutes' incubation with 1 mg/ml of p-nitrophenyl phosphate in 10% of diethanolamine-buffer of pH 9.6 at room temperature. Colour development was then measured photometrically at 410 nm, and compared with the zero value ($\Delta\epsilon$). The carrier materials used for the zero values were treated in exactly the same way, but the salt solution did not contain IgG.

| Sample 1 | Sample 2 | Sample 3 | Sample 4 | Sample 5 |
|---|---|---|---|---|
| 0.220 | 0.415 | 0.509 | 0.416 | 0.560 |

The results showed that PLA and PHB/PLA formulations with at least 5% of PLA indicated good to excellent protein affinity.

Example 3

Protein Binding to Biogenic and Biodegradable Carrier Materials With Binding at Room Temperature The experiment shown in Example 2 was repeated for some formulations, the only difference being that the incubation of the IgG solution was not carried out overnight in the refrigerator, but for 2 hours at room temperature.

|  | Sample 1 | Sample 2 | Sample 5 |
|---|---|---|---|
| $\Delta\epsilon$ | 0.210 | 0.410 | 0.520 |

The results indicated that protein binding can also take place at room temperature.

Example 4

Protein Binding to Biogenic and Biodegradable Carrier Materials and Comparison with Binding to Polystyrene To compare the affinity of proteins to biogenic, biodegradable formulations with the affinity of proteins to the polystyrene used at present, a dilution test was carried out with a stock solution of 1 μg/ml of IgG in PBS as in example 2. Samples 2 and 5 from example 1 were used as carrier as well as polystyrene.

|  | 1:50 | 1:100 | 1:200 | 1:400 |
|---|---|---|---|---|
| $\Delta\epsilon$ sample 2 | 1.053 | 0.805 | 0.659 | 0.517 |
| $\Delta\epsilon$ sample 5 | 1.145 | 1.120 | 1.011 | 0.807 |
| $\Delta\epsilon$ polystyrene | 1.156 | 1.100 | 1.000 | 0.765 |

The results showed that protein binding for the biogenic and biodegradable formulations is comparable to that for polystyrene.

Example 5

Comparing Different Blocking Reagents

To find out whether the values found in the above example were affected by the blocking reagents, polystyrene and samples 2 and 5 from example 1 were treated with the following blocking reagents:

1. Gelatine, 0.5% in PBS
2. Bovine serum albumin, 1% in PBS
3. Ovalbumin, 1% in PBS
4. Casein, 0.5% in PBS
5. Polyethylene glycol, 1% in PBS
6. Tween 20, 0,5% in PBS
7. Glycin, 1% in PBS The beads were incubated for 2 hours with the reagents. The solutions then were removed, the beads washed with distilled water, and incubated with antibody conjugated alkaline phosphatase in PBS for 60 minutes at room temperature. Measurements were made as in example 2.

|  | 1 | 2 | 3 | 4 | 5 | 6 | 7 |
|---|---|---|---|---|---|---|---|
| Δε Sample 2 | 0.60 | 0.28 | 0.36 | 0.31 | 1.0 | 0.33 | 0.65 |
| Δε Sample 5 | 0.73 | 0.35 | 0.33 | 0.41 | 1.2 | 0.32 | 0.52 |
| Δε Polystyrene | 0.62 | 0.68 | 0.70 | 0.69 | 1.2 | 0.68 | 0.73 |

The results indicated that the different blocking reagents produced values with the biogenic biodegradable carriers that were as good as or better than the values for polystyrene.

Example 6

Binding of Other Substances

Experiment 2 was repeated qualitatively with a series of different substances. The table below shows the substances and the binding. + signifies good binding, ± average binding and − poor bonding.

|  | sample 2 | sample 5 | polystyrene |
|---|---|---|---|
| IgG | + | + | + |
| IgA mouse | + | + | + |
| IgA rabbit | + | + | + |
| IgA sheep | + | + | + |
| Peroxidase obtained from horse-radish | − | − | + |
| Thyreoglobuline (TG) | + | + | + |
| Anti-TG (polyclonal) | + | + | + |
| Anti-TG (monoclonal) | ± | ± | ± |
| Streptavidine | + | + | + |

What is claimed is:

1. A method of producing a carrier for an analytical test system having increased affinity for organic substances, comprising preparing a polymer material comprising one or more water-resistant, biodegradable polylactide polymers and 0% to 95% of one or more water-resistant, biodegradable polyalcanoate polymers; and forming the polymer material into a shape of the carrier.

2. The method of claim 1 wherein the carrier is a micro titre plate, a test rod, a test tube or a test sphere.

3. The method of claim 1 wherein the polymer material further comprises one or more additives selected from the group consisting of plasticizers, dyes and nucleating agents.

4. The method of claim 1 wherein the polymer material comprises polylactate or a mixture of polylactate and polyhydroxybutyrate.

5. The method of claim 4 wherein the polymer material comprises a mixture of poylactate with 0% to 95% polyhydroxybutyrate.

6. The method of claim 4 wherein the polymer material comprises a mixture of polylactate and polyhydroxybutyrate in a ratio of 5:95 or 10:90.

7. The method of claim 4 wherein the polymer material comprises polylactate.

8. A test system comprising a carrier made from a polymer material with increased affinity for organic substances, wherein the polymer material comprises one or more water-resistant, biodegradable polylactide polymers and 0% to 95% of one or more water-resistant, biodegradable polyalcanoate polymers.

9. A test system according to claim 8 which is a micro well plate, a test rod, a test tube, or a test sphere.

10. A test system according to claim 8 wherein the polymer material further comprises one or more additives selected from the group consisting of plasticizers, dyes and nucleating agents.

11. A test system according to claim 8 wherein the polymer material comprises polylactate or a mixture of polylactate and polyhydroxybutyrate.

12. A test system according to claim 11 wherein the polymer material comprises polylactate mixed with 0% to 95% polyhydroxybutyrate.

13. A test system according to claim 11 wherein the polymer material comprises a mixture of polylactate and polyhydroxybutyrate in a ratio of 5:95 or 10:90.

14. A test system according to claim 11 wherein the polymer material comprises polylactate.

* * * * *